(12) United States Patent　　　　(10) Patent No.:　US 12,661,360 B2

Tu et al.　　　　　　　　　　　　　　(45) Date of Patent:　Jun. 23, 2026

(54) READY TO USE NON-AQUEOUS SOLUTIONS OF LAMOTRIGINE

(71) Applicant: Tulex Pharmaceuticals Inc., Cranbury, NJ (US)

(72) Inventors: Yu-Hsing Tu, West Windsor, NJ (US); Yingjun Fan, Plainsboro, NJ (US); Kalyan Kathala, Monroe, NJ (US); Ashok Perumal, South Brunswick, NJ (US); James A. Lee, West Windsor, NJ (US)

(73) Assignee: Tulex Pharmaceuticals Inc., Cranbury, NJ (US)

( * ) Notice: Subject to any disclaimer, the term of this patent is extended or adjusted under 35 U.S.C. 154(b) by 0 days.

(21) Appl. No.: 18/767,610

(22) Filed: Jul. 9, 2024

(65) Prior Publication Data

US 2025/0144106 A1　　May 8, 2025

Related U.S. Application Data

(60) Provisional application No. 63/595,974, filed on Nov. 3, 2023.

(51) Int. Cl.
*A61K 31/53*　　　(2006.01)
*A61K 9/08*　　　(2006.01)
*A61K 47/10*　　　(2017.01)

(52) U.S. Cl.
CPC ................ *A61K 31/53* (2013.01); *A61K 9/08* (2013.01); *A61K 47/10* (2013.01)

(58) Field of Classification Search
CPC ........... A61K 31/53; A61K 9/08; A61K 47/10
See application file for complete search history.

(56) References Cited

U.S. PATENT DOCUMENTS

| | | | |
|---|---|---|---|
| 10,653,626 B2 | 5/2020 | Lu et al. | |
| 2005/0238724 A1 | 10/2005 | Aronhime et al. | |
| 2020/0046716 A1 * | 2/2020 | Mehta ................. | A61K 9/0053 |
| 2020/0375995 A1 | 12/2020 | Sudhakar et al. | |
| 2021/0069109 A1 | 3/2021 | Sudhakar et al. | |

FOREIGN PATENT DOCUMENTS

| | | | | |
|---|---|---|---|---|
| CN | 104873461 A | 9/2015 | | |
| MX | PA03008841 A | * | 4/2005 | ............. A61K 90/00 |
| WO | 94/20108 A1 | 9/1994 | | |

OTHER PUBLICATIONS

S. Soltanpour, et al. Solubility of Lamotrigine in binary and ternary mixtures of PEGs 200, 400, and 600 with ethanol, PG, and water at 298.2 K, Chemical Engineering Communications, 2013, vol. 200, pp. 1443-1456, https://api.semanticscholar.org/CorpusID:95136658. (Year: 2013).*

F. Ghaderi, et al. Latin American Journal of Pharmacy, 2014, vol. 33, IS. 8, pp. 1392-1396, Solubility of Lamotrigine in Propylene Glycol plus Ethanol and Their Ternary Aqueous Mixtures | Health & Environmental Research Online (HERO) | US EPA (Year: 2014).*

A. Sheikhi-Sovari, et al. Dissolution and thermodynamic study of lamotrigine in propylene glycol+1-propanol mixtures. Physics and Chemistry of Liquids, Oct. 2023, 62(1), 34-43. https://doi.org/10.1080/00319104.2023.2264455. (Year: 2023).*

S. Neerumalla, et al. (Current Medicine Research and Practice 12(4):p. 157-161, Jul.-Aug. 2022, DOI: 10.4103/cmrp.cmrp_45_22. (Year: 2022).*

Lamotrigine drug information, MedlinePlus, 2021, https://medlineplus.gov/druginfo/meds/a695007.html. (Year: 2021).*

Keen et al., "Degradation pathways of lamotrigine under advanced treatment by direct UV photolysis, hydroxyl radicals, and ozone," Chemosphere, vol. 117, pp. 316-323 (2014).

Soltanpour et al., "Solubility of Lamotrigine in Binary and Ternary Mixtures of PEGs 200, 400, and 600 with Ethanol, PG, and Water at 298.2K," Chem. Eng. Comm. vol. 200, pp. 1443-1456 (2013).

Nahata et al., "Stability of lamotrigine in two extemporaneously prepared oral suspensions at 4 and 25 °C," Am. J. Health-Syst. Pharm., vol. 56, pp. 240-242 (1999).

International Search Report and Written Opinion dated Oct. 30, 2024 for International Application No. PCT/US2024/037217 (14 pages).

* cited by examiner

*Primary Examiner* — James H Alstrum-Acevedo
*Assistant Examiner* — Manahil Mirghani Ali Abdalhameed
(74) *Attorney, Agent, or Firm* — Venable LLP

(57) ABSTRACT

Disclosed are ready to use non-aqueous solutions of lamotrigine. The lamotrigine is dissolved in a solvent, wherein the solvent comprises propylene glycol and optionally at least one co-solvent, and wherein if water is present in the ready to use non-aqueous solution, the water is not at least one co-solvent. Also disclosed are methods for treating a neurological disorder or a mental disorder by administering the ready to use non-aqueous solutions of lamotrigine, processes for preparing ready to use non-aqueous solutions of lamotrigine, and kits containing lamotrigine to prepare ready to use non-aqueous solutions of lamotrigine.

30 Claims, 1 Drawing Sheet

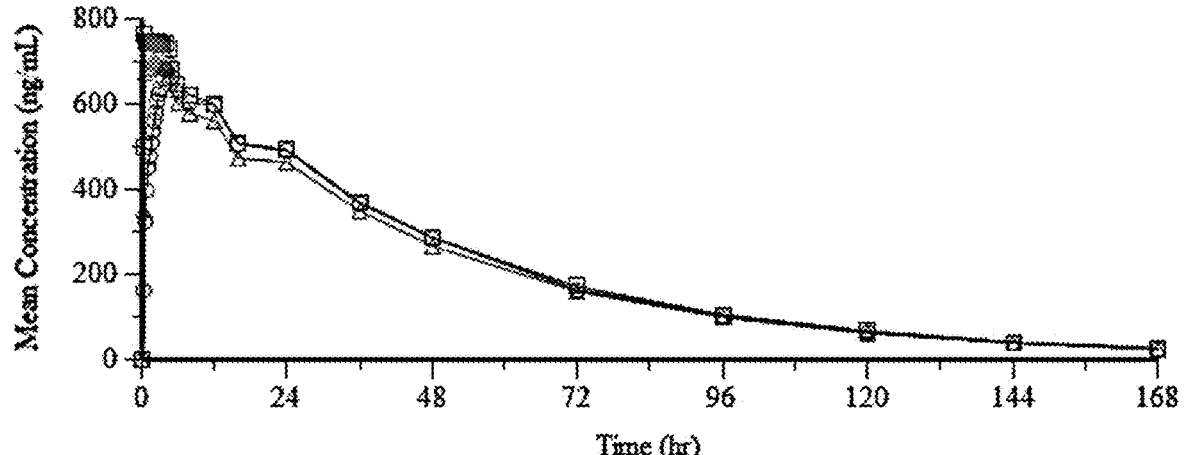

READY TO USE NON-AQUEOUS SOLUTIONS OF LAMOTRIGINE

CROSS REFERENCE TO RELATED APPLICATIONS

This application claims the benefit of U.S. Provisional Application No. 63/595,974, filed Nov. 3, 2023, the disclosure of which is incorporated herein by reference in its entirety.

FIELD OF THE DISCLOSURE

This disclosure relates to ready to use non-aqueous solutions of lamotrigine, methods for treating a neurological disorder or a mental disorder with the ready to use non-aqueous solutions of lamotrigine, processes for preparing the ready to use non-aqueous solutions of lamotrigine, and kits comprising the ready to use non-aqueous solutions of lamotrigine.

BACKGROUND

Lamotrigine, also known as 3,5-diamino-6-(2,3-dichloro-phenyl)-1,2,4-triazine, is an active pharmaceutical agent useful for treating various indications such as epilepsy and bipolar disorder. For epilepsy, it is used to treat partial seizures, primary and secondary tonic-clonic seizures, and seizures associated with Lennox-Gastaut syndrome. Lamotrigine also acts as a mood stabilizer. Chemically unrelated to other anti-convulsants (due to lamotrigine being a phenyltriazine), lamotrigine has relatively few side-effects and does not require blood monitoring in monotherapy.

Lamotrigine is a BCS class II drug with low solubility and high permeability. Oral administration is associated with a delayed onset of the desired pharmacological action as lamotrigine is poorly soluble in water, which results in a low rate of dissolution of the drug in aqueous media including biological fluids such as gastrointestinal fluid.

While lamotrigine may be administered as a solid, there is a need for liquid formulations as well. Currently, there are no liquid formulations of lamotrigine commercially available and, as a result, hospital pharmacists often crush lamotrigine tablets for administration to pediatric patients who cannot swallow tablets.

SUMMARY

The present disclosure provides a ready to use non-aqueous solution comprising lamotrigine dissolved in a solvent, wherein the solvent comprises propylene glycol and optionally at least one co-solvent, and wherein if water is present in the ready to use non-aqueous solution, the water is not this at least one co-solvent.

The present disclosure also provides a ready to use non-aqueous solution comprising lamotrigine dissolved in a solvent, wherein the solvent comprises polyethylene glycol or glycerin and optionally at least one co-solvent, and wherein if water is present in the ready to use non-aqueous solution, the water is not this at least one co-solvent.

The present disclosure also provides a method for treating a neurological disorder or a mental disorder in a subject in need thereof, comprising administering to the subject the disclosed ready to use non-aqueous solutions of lamotrigine, wherein the ready to use non-aqueous solution includes a therapeutically effective amount of lamotrigine.

The present disclosure also provides processes for preparing the disclosed ready to use non-aqueous solutions of lamotrigine, comprising: mixing lamotrigine with the solvent to dissolve lamotrigine in the solvent.

The present disclosure also provides a kit comprising: a first container comprising lamotrigine; and a second container comprising a solvent comprising propylene glycol and optionally at least one co-solvent, wherein contents of the first container and the second container are, upon use, mixed to form a disclosed ready to use non-aqueous solution, wherein if water is present in the ready to use non-aqueous solution, the water is not this at least one co-solvent.

The present disclosure also provides a kit comprising: a first container comprising lamotrigine; and a second container comprising a solvent comprising polyethylene glycol or glycerin and optionally at least one co-solvent, wherein contents of the first container and the second container are, upon use, mixed to form a disclosed ready to use non-aqueous solution, wherein if water is present in the ready to use non-aqueous solution, the water is not this at least one co-solvent.

BRIEF DESCRIPTION OF THE FIGURES

The FIGURE is exemplary in nature and is not to be construed in a limiting manner with respect to the appended claims.

FIGURE is a graphical representation showing a mean plasma concentration versus time, according to embodiments of the disclosure.

DETAILED DESCRIPTION

Liquid formulations can have different forms. One well-known type of liquid formulations is a suspension. For lamotrigine, however, suspensions may be undesirable because it has now been discovered they may have, e.g., increased dosage variability and/or there is a need to remix or resuspend any solids formed. An additional drawback of lamotrigine suspensions that has now been discovered is a difficultly in maintaining chemical stability of the drug in the dosage form.

Another well-known type of liquid formulations is a solution. However, because lamotrigine is difficult to dissolve or stabilize in a water-based medium due to, e.g., a tendency for lamotrigine to form suspensions and/or precipitates in the presence of water, there are considerable impediments in preparing suitable lamotrigine solutions.

Attempts have been made to develop liquid solutions of lamotrigine. However, if water was used as one of the solvents, such formulations could accommodate only a small concentration of lamotrigine due to its very limited solubility. Moreover, such formulations lack sufficient stability, leading to formation of suspensions and/or precipitates.

Conventionally, LAMICITAL (lamotrigine) tablets are suggested to be administered for ages 2 years and above, where the dosage is titrated based on the body weight of the subject. When LAMICITAL (lamotrigine) is prescribed with other concomitant medications, it becomes even more difficult to titrate the correct dosage. Currently, there are no ready to use lamotrigine-based oral liquid medicaments available in the market.

Advantageously, the present disclosure provides a ready to use non-aqueous lamotrigine solution. This ready to use non-aqueous lamotrigine solution is not a suspension and can accommodate a considerably higher concentration of lamotrigine than was previously possible. Moreover, even in the event some water is present in this ready to use non-aqueous solution, it is not used as a solvent. That is, water is not a co-solvent, and the ready to use non-aqueous lamotrigine solution as disclosed herein can tolerate the presence of a certain amount of water and still maintain the ability to retain a high concentration of lamotrigine without forming a precipitate and/or a suspension.

In addition, the ready to use non-aqueous lamotrigine solution helps to mitigate errors associated with titration or dilution so that a precise dosage can be administered, especially for pediatric subjects. Also, the ready to use non-aqueous lamotrigine solution provides improved swallowability for subjects that may have difficulty swallowing conventional tablets or capsules. Further, the ready to use non-aqueous lamotrigine solution is capable for meeting individual needs of the subject due to the flexibility of titrating the accurate dosage.

As used herein, the term "solution" refers to a liquid single phase homogenous mixture containing two or more substances. In the mixture, the term "solute" is a substance dissolved in another substance, referred to as the term "solvent." For example, propylene glycol, a solvent, dissolves lamotrigine, a solute. As known in the art, particles of the solute are not visible in the solution and does not cause light to scatter. The dissolved solute cannot be separated by mechanical filtration. The solute will not precipitate unless added in excess of the mixture's solubility. If more than one solvent is present in a solution, each solvent may be referred to as a "co-solvent," and each co-solvent or a combination of co-solvents may individually or collectively be referred to as a "solvent." Solutions include aqueous solutions and non-aqueous solutions. Solutions do not include suspensions.

As used herein, the term "suspension" refers to a liquid phase heterogeneous mixture that contains solid particles that can be sufficiently large for sedimentation. The solid particles can be visible and cause light to scatter. The solid particles are not dissolved in the liquid phase fluid.

As used herein, the term "dissolve" refers to the solute being solvated by the solvent (and optional co-solvents). As known in the art, if the attractive forces between the solvent (and optional co-solvents) and solute molecules are greater than the attractive forces holding the solute molecules together, the solvent molecules pull the solute molecules apart and surround them. The surrounded solute molecules move away from the solute and out into the solution.

As used herein, the term "aqueous solution" refers to a solution where water is a solvent or an optional co-solvent.

As used herein, the term "non-aqueous solution" refers to a solution where water is not a solvent and not an optional co-solvent. The non-aqueous solution may include water, but the water molecules do not participate in dissolving the solute.

As used herein, the term "ready to use" non-aqueous solution refers to a non-aqueous solution-based medicament that is readily suitable for direct administration to a subject without undergoing further manipulation (e.g., dilution). Such a "ready to use" non-aqueous solution helps reduce the errors associated with the preparation and administration of the medications.

As used herein, the term "standard temperature and pressure" refers to 15-25° C. and 1 atm.

As used herein, a "stable solution" is a solution in which particles do not settle down under the effect of gravity over a certain amount of time, for example, at least 7 days. Because particles of the solute are not visible in the solution and does not cause light to scatter, the stability of the solution can be quantified by turbidity, which is the opaqueness of a fluid caused by particles that may be present in the solution. Turbidity is expressed using Nephelometric Turbidity Units (NTU).

As used herein, the term "about" refers to plus or minus 10% of the indicated value. Unless otherwise stated, weight percentages are provided based on the total amount of the composition in which they are described.

As used herein, the singular forms "a," "an," and "the" include plural referents unless stated otherwise.

As used herein, the terms "therapeutically effective amount" is intended to mean that the ready to use non-aqueous solutions of lamotrigine will elicit the biological or medical response of a tissue, a system, animal, or human that is being sought by a researcher, veterinarian, medical doctor or other clinician. In a preferred embodiment, the term "therapeutically effective amount" means an amount that alleviates at least one clinical symptom in a human patient. The terms "prophylactically effective (or efficacious) amount" and similar descriptions such as "an amount efficacious for prevention" are intended to mean that amount that will prevent or reduce the risk of occurrence of the biological or medical event that is sought to be prevented in a tissue, a system, animal or human by a researcher, veterinarian, medical doctor or other clinician.

As used herein, the disclosure of numerical ranges within this specification is considered to be a disclosure of all numerical values and ranges within that range. For example, if a range is from about 1 to about 50, it is deemed to include, for example, 1, 7, 34, 46.1, 23.7, 50 or any other value or range within the range. Moreover, as used herein, the term "at least" includes the stated number, e.g., "at least 50" includes 50.

As used herein, the term "administration" and variants thereof (e.g., "administering") in reference to an active agent of the disclosure means providing the active agent to a subject in need of treatment. Administering of an active agent of the disclosure to the subject includes both self-administration and administration to the subject by another, including a medical professional. Administration may be via any common route, and in forms suitable for each administration route. Such routes include, but are not limited to, parenteral (e.g., subcutaneous, intramuscular, intraperitoneal or intravenous) and oral. For example, the administration can be carried out orally after fasting, or the administration can be carried out orally after a meal.

As used herein, "fasting" refers to abstaining from all types of food and/or fluids for a certain period of time before and/or after dosing. For example, fasting may refer to abstaining from food for at least ten hours prior to dosing until at least four hours after dosing. Water may be restricted from at least 1 hour prior to dosing until at least 1 hour post-dosing (no fluid, except water given with dosing, where needed).

As used herein, a "healthy adult" refers to a human subject who is 18 years or older and does not have any medical conditions or diseases for which lamotrigine is being tested or administered for treatment.

As used herein, "treat", "treating", or "treatment" includes treating for the purpose of curing or ameliorating a neurological disorder or a mental disorder, or for the purpose of suppressing the progression, occurrence, or recurrence of the neurological disorder or the mental disorder or alleviating one or more of the associated symptoms.

As used herein, "administered every day" or "daily" or "once a day" or "once a day on each day" includes an administration schedule based on a regimen in which dosing is performed on every day of a treatment cycle (i.e., treatment period). For example, an active ingredient may be administered every day of a treatment cycle. In some embodiments, a "drug holiday" may be provided as each treatment cycle ends. In some embodiments, an active agent is administered once during a treatment cycle.

As used herein, the "treatment cycle" refers to the period of time during which the administration according to the methods of the disclosure takes place. During a treatment cycle, the active agent of the method is administered sequentially or simultaneously as described herein.

As used herein, "administered intermittently" is not particularly limited as long as the conditions of at least twice during the treatment cycle and an administration interval of at least one day between dosing (the number of days between a certain day of administration and the next day of administration) are satisfied.

As used herein, "bioequivalence" refers to the absence of a significant difference in the rate and extent to which the active ingredient in pharmaceutical equivalents becomes available at the site of drug action when administered at the same molar dose under similar conditions in an appropriately designed pharmacokinetic study. For example, two products are bioequivalent if the 90% confidence interval (CI) of the relative mean $C_{max}$, $AUC_t$ and $AUC_i$ of the ready to use non-aqueous solution to the reference commercially available product is within 80% to 125% in the fasting state.

As used herein, "$C_{max}$" refers to the maximum measured plasma concentration.

As used herein, "$AUC_t$" refers to the area under the plasma concentration versus time curve from time zero to the last quantifiable concentration.

As used herein, "$AUC_i$" refers to the area under the plasma concentration versus time curve from time zero to infinity.

The present disclosure provides ready to use non-aqueous solutions including lamotrigine dissolved in a solvent, wherein the solvent includes propylene glycol and optionally at least one co-solvent, and wherein if water is present in the ready to use non-aqueous solution, the water is not this at least one co-solvent.

The lamotrigine in the ready to use non-aqueous solutions as disclosed herein is dissolved in one or more non-aqueous solvents. Non-limiting examples of the ready to use non-aqueous solvent include at least one alcohol and/or at least one diol such as propylene glycol, glycerin, polypropylene glycol, polyethylene glycol, and ethanol.

In some embodiments, the solvent includes propylene glycol. In some embodiments, the solvent may optionally include at least one co-solvent. This at least one co-solvent includes at least one selected from the group consisting of glycerin, polypropylene glycol, polyethylene glycol, and ethanol.

In some embodiments, the ready to use non-aqueous solution includes a solvent and the solvent includes propylene glycol. Optionally, the solvent of the ready to use non-aqueous solution further includes a co-solvent. The co-solvent can be glycerin.

In alternate embodiments, the solvent includes polyethylene glycol. In alternate embodiments, the solvent includes glycerin. In alternate embodiments, the solvent includes polyethylene glycol and glycerin. Optionally, the solvent may further include at least one co-solvent. The at least one co-solvent includes at least one selected from the group consisting of polypropylene glycol and ethanol.

In some embodiments, the ready to use non-aqueous solutions of lamotrigine include various amounts of lamotrigine. In some embodiments, the ready to use non-aqueous solution has a lamotrigine concentration from about 0.4 mg/mL to about 40 mg/mL or any sub-range thereof. For example, in some embodiments, the ready to use non-aqueous solution has a lamotrigine concentration of from about 0.01 mg/mL to about 40 mg/mL, about 0.05 mg/mL to about 40 mg/mL, about 0.1 mg/mL to about 40 mg/mL, about 0.2 mg/mL to about 40 mg/mL, about 0.3 mg/mL to about 40 mg/mL, about 0.01 mg/mL to about 35 mg/mL, about 0.05 mg/mL to about 35 mg/mL, about 0.1 mg/mL to about 35 mg/mL, about 0.1 mg/mL to about 35 mg/mL, about 0.2 mg/mL to about 35 mg/mL, about 0.3 mg/mL to about 35 mg/mL, about 0.4 mg/mL to about 35 mg/mL, about 0.5 mg/mL to about 35 mg/mL, about 0.5 mg/mL to about 40 mg/mL, about 1 mg/mL to about 40 mg/mL, about 0.4 mg/mL to about 30 mg/mL, about 0.4 mg/mL to about 20 mg/mL, about 0.4 mg/mL to about 10 mg/mL, about 0.4 mg/mL to about 5 mg/mL, about 0.4 mg/mL to about 2 mg/mL, about 0.5 mg/mL to about 30 mg/mL, about 0.5 mg/mL to about 20 mg/mL, about 0.5 mg/mL to about 10 mg/mL, about 0.5 mg/mL to about 5 mg/mL, about 0.5 mg/mL to about 2 mg/mL, about 1 mg/mL to about 30 mg/mL, about 1 mg/mL to about 20 mg/mL, about 1 mg/mL to about 10 mg/mL, about 15 mg/mL to about 5 mg/mL, about 1 mg/mL to about 2 mg/mL, about 10 mg/mL to about 40 mg/mL, about 10 mg/mL to about 30 mg/mL, about 10 mg/mL to about 20 mg/mL, about 15 mg/mL to about 25 mg/mL, about 16 mg/mL to about 24 mg/mL, about 17 mg/mL to about 23 mg/mL, about 18 mg/mL to about 22 mg/mL, or about 19 mg/mL to about 21 mg/mL. In some embodiments, the ready to use non-aqueous solution has a lamotrigine concentration of about 20 mg/mL.

In some embodiments, the ready to use non-aqueous solutions of lamotrigine may include water. However, if water is present in the ready to use non-aqueous solution, it is neither the sole solvent nor at least one of the co-solvents.

As such, the ready to use non-aqueous solutions of lamotrigine as disclosed herein have a water tolerance, whereby the ready to use non-aqueous solution does not form a precipitate or suspension even when some water is present. For example, in some embodiments, a ready to use non-aqueous solution may include up to about 20% w/w, or any sub-range thereof, of water and not form a precipitate or suspension, even when stored at standard temperature and pressure for at least 7 days.

In some embodiments, the ready to use non-aqueous solution has a water content equal to or less than about 20% w/w, equal to or less than about 15% w/w, equal to or less than about 10% w/w, equal to or less than about 5% w/w, equal to or less than about 4% w/w, equal to or less than about 3% w/w, equal to or less than about 2% w/w, equal to or less than about 1% w/w, equal to or less than about 0.9% w/w, equal to or less than about 0.8% w/w, equal to or less than about 0.7% w/w, equal to or less than about 0.6% w/w, equal to or less than about 0.5% w/w, equal to or less than about 0.4% w/w, equal to or less than about 0.3% w/w, equal to or less than about 0.2% w/w, equal to or less than about 0.1% w/w, equal to or less than about 0.01% w/w, equal to or less than about 0.001% w/w, equal to or less than about 0.0001% w/w, equal to or less than about 0.00001% w/w, or equal to or less than about 0.000001% w/w of the ready to use non-aqueous solution, or any concentration therebetween.

In some embodiments, the ready to use non-aqueous solution has a pH meter reading from about 7 to about 8, or any sub-range thereof. For example, in some embodiments, the ready to use non-aqueous solution has a pH meter reading from about 7 to about 8, about 7.2 to about 8, or about 7.5 to about 7.8. In some embodiments, the ready to use non-aqueous solution has a pH meter reading of about 7.53. The pH meter reading of a ready to use non-aqueous solution may be determined by various standard techniques, such as by using a pH meter using an electrode suitable for aqueous solutions or non-aqueous solutions.

In some embodiments, the ready to use non-aqueous solution has a density from about 1.0 g/mL to about 1.3 g/mL or any sub-range thereof. For example, in some embodiments, the ready to use non-aqueous solution has a density from about 1.0 g/mL to about 1.3 g/mL, about 1.1 g/mL to about 1.3 g/mL, about 1.2 g/mL to about 1.3 g/mL, about 1.0 g/mL to about 1.2 g/mL, about 1.0 g/mL to about 1.1 g/mL, or about 1.1 g/mL to about 1.2 g/mL.

In some embodiments, the ready to use non-aqueous solution has a viscosity from about 50 centipoise to about 500 centipoise or any sub-range thereof. For example, in some embodiments, the ready to use non-aqueous solution has a viscosity from about 50 centipoise to about 500 centipoise, about 50 centipoise to about 400 centipoise, about 50 centipoise to about 300 centipoise, about 100 centipoise to about 500 centipoise, about 200 centipoise to about 500 centipoise, about 200 centipoise to about 400 centipoise, or 200 centipoise to about 300 centipoise. The viscosity of the ready to use non-aqueous solution may be determined by using a commercial viscometer, such as Viscometer DVEELVTJ0. The following example conditions can be implemented when using the commercial viscometer: S62 tip, 30 rpm, FB-100-50 beaker, 40 mL sample. The viscosity is determined when the reading of the commercial viscometer is stabilized.

In some embodiments, the ready to use non-aqueous solution has a turbidity ranging from 0 NTU to 20 NTU or any sub-range thereof. For example, in some embodiments, the ready to use non-aqueous solution has a turbidity ranging from about 0 NTU to about 20 NTU, about 0 NTU to about 15 NTU, about 0 NTU to about 10 NTU, or about 0 NTU to about 5 NTU. The turbidity of the ready to use non-aqueous solution can be measured by standard procedures known in the art.

In some embodiments, the ready to use non-aqueous solution exists in liquid phase at standard temperature and pressure. In some embodiments, the ready to use non-aqueous lamotrigine solution is a clear and colorless to light yellow liquid. In some embodiments, the ready to use non-aqueous lamotrigine solution does not form a precipitate when stored at standard temperature and pressure for at least 7 days.

For example, in some embodiments, the ready to use non-aqueous solution is a stable ready to use non-aqueous solution that does not form a precipitate and/or does not become a suspension when stored at standard temperature and pressure for at least 7 days, is a clear and colorless to light yellow liquid, and/or has a turbidity ranging from about 0 NTU to about 20 NTU, about 0 NTU to about 15 NTU, about 0 NTU to about 10 NTU, or about 0 NTU to about 5 NTU. In some embodiments, the ready to use non-aqueous solutions having propylene glycol to glycerin weight ratios of 10:90, 90:10, 25:75, and 40:60, demonstrate sufficient stability.

The ready to use non-aqueous solutions of lamotrigine may contain various ratios of solvent and co-solvents. In some embodiments, the ready to use non-aqueous solution has a weight ratio of propylene glycol to glycerin from about 100:0 to about 10:90 or any subrange thereof. For example, in some embodiments, the ready to use non-aqueous solution has a weight ratio of propylene glycol to glycerin from about 100:0 to about 10:90, about 90:10 to about 10:90, about 80:20 to about 20:80, about 70:30 to about 30:70, about 60:40 to about 40:60, or about 45:55 to about 55:45.

The ready to use non-aqueous solutions of lamotrigine may contain various amounts of solvent such as propylene glycol. In some embodiments, the ready to use non-aqueous solution has a propylene glycol content of about 0% to about 100% w/w, or any sub-range thereof, of the ready to use non-aqueous solution. For example, in some embodiments, the ready to use non-aqueous solution has a propylene glycol content of about 10% to about 87% w/w, about 15% to about 85% w/w, about 20% to about 80% w/w, about 25% to about 75% w/w, about 30% to about 70% w/w, about 45% to about 55% w/w, about 15% to about 87% w/w, about 20% to about 87% w/w, about 25% to about 87% w/w, about 35% to about 87% w/w, about 45% to about 87% w/w, about 55% to about 87% w/w, about 65% to about 87% w/w, or about 70% to about 87% w/w of the ready to use non-aqueous solution.

The ready to use non-aqueous solutions of lamotrigine may contain various amounts of glycerin. In some embodiments, the ready to use non-aqueous solution has a glycerin content of about 0% to about 100% w/w, or any sub-range thereof, of the ready to use non-aqueous solution. For example, in some embodiments, the ready to use non-aqueous solution has a glycerin content of about 11% to about 88% w/w, about 11% to about 85% w/w, about 11% to about 80% w/w, about 11% to about 75% w/w, about 11% to about 70% w/w, about 11% to about 60% w/w, about 11% to about 50% w/w, about 11% to about 40% w/w, about 11% to about 30% w/w, about 15% to about 88% w/w, about 20% to about 88% w/w, about 30% to about 88% w/w, about 40% to about 88% w/w, about 50% to about 88% w/w, or about 60% to about 88% w/w of the ready to use non-aqueous solution. In some embodiments, the ready to use non-aqueous solution includes, in addition to glycerin, a co-solvent that is polypropylene glycol and/or ethanol.

The ready to use non-aqueous solutions of lamotrigine may contain various types of polyethylene glycol. For example, in some embodiments, the polyethylene glycol exists in liquid phase at standard temperature and pressure. In some embodiments, the polyethylene glycol has an average molecular weight of equal to or less than about 1000 g/mol or any sub-range thereof. For example, in some embodiments, the polyethylene glycol has an average molecular weight ranging from about 100 g/mol to about 1000 g/mol, about 200 g/mol to about 800 g/mol, about 200 g/mol to about 600 g/mol, equal to or less than about 600 g/mol, equal to or less than about 500 g/mol, equal to or less than about 400 g/mol, or equal to or less than about 300 g/mol. In some embodiments, the polyethylene glycol is at least one selected from the group consisting of polyethylene glycol 600 (PEG-600), polyethylene glycol 500 (PEG-500), polyethylene glycol 400 (PEG-400), polyethylene glycol 300 (PEG-300), and polyethylene glycol 200 (PEG-200).

The ready to use non-aqueous solutions of lamotrigine may contain various additives such as antioxidants, buffers, flavorants, coloring agents, and/or preservatives. Antioxidants include free-radical scavengers and scavengers of reactive oxygen species such as, for example, 3-tert-butyl-4-hydroxyanisole, butylated hydroxytoluene, and citric acid. Buffers include combinations of acids and bases that have a pH buffering capacity. Some buffers include, for example, citrate, phosphate, acetate, borate, ethylenediaminetetraacetate (EDTA), conjugate acids thereof, and combinations thereof. Preservatives include compounds that increase the usable shelf life of the pharmaceutical composition. For example, some preservatives are antioxidants, some preservatives are antifungal agents, and some preservatives are antibacterial agents. Flavorants can be added to improve the taste of the ready to use non-aqueous lamotrigine solutions and include, for example, ethyl maltol, sucralose, cherry flavor. Coloring agents can be added to improve the visual appearance of the ready to use non-aqueous lamotrigine solutions and include, for example, 2-(2-Quinolyl)-1,3-indandione disulfonic acid disodium salt (D&C Yellow #10). In some embodiments, the ready to use non-aqueous solution comprises at least one additive selected from the group consisting of 3-tert-butyl-4-hydroxyanisole, citric acid, ethylenediaminetetraacetic acid, ethyl maltol, propylparaben, and methylparaben.

In some embodiments, the ready to use non-aqueous solution contains equal to or less than about 10 weight % of sugar (for example, sucrose and sucralose) by total weight of the ready to use non-aqueous solution or any subrange thereof. For example, in some embodiments, the ready to use non-aqueous solution contains equal to or less than about 10 weight %, equal to or less than about 5 weight %, equal to or less than about 3 weight %, or equal to or less than about 1 weight % of sugar by total weight of the ready to use non-aqueous solution. In some embodiments, the ready to use non-aqueous solution does not contain sugar.

The ready to use non-aqueous solutions of lamotrigine can be made by various processes. For example, in some embodiments, the ready to use non-aqueous solution comprising lamotrigine is prepared by mixing lamotrigine with the solvent to dissolve lamotrigine in the solvent. The mixing step may be performed at various temperatures for various durations using various tools. For example, the mixing step may be performed at room temperature using any standard mixing device for any duration so long as the lamotrigine becomes dissolved in the solvent.

The ready to use non-aqueous solutions of lamotrigine can be prepared in various kits. In some embodiments, a kit includes a first container comprising lamotrigine; and a second container including a solvent including propylene glycol and optionally at least one co-solvent, wherein contents of the first container and the second container are, upon use, mixed to form a ready to use non-aqueous solution including lamotrigine, wherein if water is present in the ready to use non-aqueous solution, the water is not this at least one co-solvent.

In alternate embodiments, a kit includes a first container including lamotrigine; and a second container including a solvent comprising polyethylene glycol or glycerin and optionally at least one co-solvent, wherein contents of the first container and the second container are, upon use, mixed to form a ready to use non-aqueous solution comprising lamotrigine, wherein if water is present in the ready to use non-aqueous solution, the water is not at least one co-solvent.

In some embodiments, at least one co-solvent includes at least one selected from the group consisting of glycerin, polypropylene glycol, polyethylene glycol, and ethanol. In some embodiments, the co-solvent comprises glycerin. In some embodiments, at least one co-solvent comprises polypropylene glycol and/or ethanol.

The kit may include a container for containing separate compositions such as a divided bottle or a divided foil packet. Additional examples of containers include syringes, boxes and bags. In some embodiments, the kit includes directions for the use of the separate components. The kit form is particularly advantageous when the separate components are administered in different dosage forms (e.g., oral and parenteral), are administered at different dosage intervals, or when titration of the individual components of the combination is desired by the prescribing health care professional.

The ready to use non-aqueous solutions of lamotrigine may be used in methods for treating a neurological disorder or a mental disorder. In some embodiments, a method for treating a neurological disorder or a mental disorder in a subject in need thereof comprises administering to the subject a therapeutically effective amount of the ready to use non-aqueous solution.

Neurological disorders and mental disorders include, for example, epilepsy, drug-resistant focal epilepsy, tonic-clonic seizures, absence seizure, myoclonic seizure, atonic seizures, Lennox-Gastaut syndrome, bipolar disorder (such as bipolar I disorder and bipolar II disorder), depression, schizophrenia, peripheral neuropathy, trigeminal neuralgia, cluster headaches, migraines, visual snow, neuropathic pain, obsessive-compulsive disorder, depersonalization disorder, hallucinogen persisting perception disorder, schizoaffective disorder, borderline personality disorder, post-traumatic stress disorder, attention deficit hyperactivity disorder, dementia, cognitive disorders, and combinations thereof.

The dosage regimen utilizing the ready to use non-aqueous solution of lamotrigine is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of a neurological disorder or a mental disorder, and a prophylactically effective amount, e.g., for prevention of a neurological disorder or a mental disorder.

For administration to a human in, for example, the curative or prophylactic treatment of the conditions and disorders identified herein, the ready to use non-aqueous solution may be administered such that the dosage of lamotrigine is about 0.05 mg/kg/day to about 50 mg/kg/day, or at least 0.05 mg/kg, or at least 0.08 mg/kg, or at least 0.1 mg/kg, or at least 0.2 mg/kg, or at least 0.3 mg/kg, or at least 0.4 mg/kg, or at least 0.5 mg/kg, and any amount therebetween, to about 50 mg/kg or less, or about 40 mg/kg or less, or about 30 mg/kg or less, or about 20 mg/kg or less, or about 10 mg/kg or less and any amount therebetween, which can be, for example, about 2.5 mg/day (0.5 mg/kg×5 kg) to about 5000 mg/day (50 mg/kg×100 kg). For example, dosages of the compounds can be about 0.1 mg/kg/day to about 50 mg/kg/day, or about 0.05 mg/kg/day to about 10 mg/kg/day, or about 0.05 mg/kg/day to about 5 mg/kg/day, or about 0.05 mg/kg/day to about 3 mg/kg/day, or about 0.07 mg/kg/day to about 3 mg/kg/day, or about 0.09 mg/kg/day to about 3 mg/kg/day, or about 0.05 mg/kg/day to about 0.1 mg/kg/day, or about 0.1 mg/kg/day to about 1 mg/kg/day, or about 1 mg/kg/day to about 10 mg/kg/day, or about 1 mg/kg/day to about 5 mg/kg/day, or about 1 mg/kg/day to about 3 mg/kg/day, or about 3 mg/day to about 500 mg/day, or about 5 mg/day to about 250 mg/day, or about 10 mg/day to about 100 mg/day, or about 3 mg/day to about 10 mg/day, or about 100 mg/day to about 250 mg/day. Such doses may be administered in a single dose or may be divided into multiple doses.

In some embodiments, the therapeutically effective amount of lamotrigine is from about 2 mg to about 700 mg, or any sub-range thereof. For example, in some embodiments, the therapeutically effective amount of lamotrigine is from about 1 mg to about 1000 mg, from about 1 mg to about 900 mg, from about 1 mg to about 800 mg, from about 1 mg to about 700 mg, from about 1 mg to about 600 mg, from about 1 mg to about 500 mg, from about 1 mg to about 400 mg, from about 1 mg to about 300 mg, from about 1 mg to about 200 mg, from about 1 mg to about 100 mg, from about 2 mg to about 1000 mg, from about 2 mg to about 900 mg, from about 2 mg to about 800 mg, from about 2 mg to about 700 mg, from about 2 mg to about 600 mg, from about 2 mg to about 500 mg, from about 2 mg to about 400 mg, from about 2 mg to about 300 mg, from about 2 mg to about 200 mg, from about 2 mg to about 100 mg, from about 5 mg to about 1000 mg, from about 5 mg to about 900 mg, from about 5 mg to about 800 mg, from about 5 mg to about 700 mg, from about 5 mg to about 600 mg, from about 5 mg to about 500 mg, from about 5 mg to about 400 mg, from about 5 mg to about 300 mg, from about 5 mg to about 200 mg, from about 5 mg to about 100 mg, from about 10 mg to about 1000 mg, from about 10 mg to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, from about 10 mg to about 80 mg, from about 10 mg to about 60 mg, from about 20 mg to about 1000 mg, from about 20 mg to about 900 mg, from about 20 mg to about 800 mg, from about 20 mg to about 700 mg, from about 20 mg to about 600 mg, from about 20 mg to about 500 mg, from about 20 mg to about 400 mg, from about 20 mg to about 300 mg, from about 20 mg to about 200 mg, from about 20 mg to about 100 mg, from about 20 mg to about 80 mg, from about 20 mg to about 60 mg, from about 40 mg to about 1000 mg, from about 40 mg to about 900 mg, from about 40 mg to about 800 mg, from about 40 mg to about 700 mg, from about 40 mg to about 600 mg, from about 40 mg to about 500 mg, from about 40 mg to about 400 mg, from about 40 mg to about 300 mg, from about 40 mg to about 200 mg, from about 40 mg to about 100 mg, from about 40 mg to about 80 mg, or from about 40 mg to about 60 mg. In some embodiments, the therapeutically effective amount of lamotrigine is about 25 mg, about 50 mg, about 100 mg, about 200 mg, about 300 mg, about 400 mg, or about 500 mg.

The ready to use non-aqueous solutions of lamotrigine can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition. Administering of the drug to the subject includes both self-administration and administration to the patient by another person. The subject may be in need of, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

The present disclosure therefore also provides ready to use non-aqueous solutions of lamotrigine for use as pharmaceuticals, their use for treating a neurological disorder or a mental disorder, and in particular their use in the therapy and prophylaxis of the above-mentioned diseases or disorders as well as their use for preparing medicaments for these purposes.

In some embodiments, the ready to use non-aqueous solutions of lamotrigine are bioequivalent to commercially available products containing lamotrigine. Non-limiting examples of commercially available products containing lamotrigine include LAMICITAL tablets.

In some embodiments, the administration of the ready to use non-aqueous solutions of lamotrigine results in a $C_{max}$ value from about 800 ng/mL to about 1,000 ng/ml of lamotrigine in the subject, or any sub-range thereof. For example, in some embodiments, the administration of the ready to use non-aqueous solutions of lamotrigine results in a $C_{max}$ value from about 100 ng/ml to about 2,000 ng/mL, from about 100 ng/mL to about 1,800 ng/ml, from about 100 ng/ml to about 1,600 ng/mL, from about 100 ng/mL to about 1,400 ng/mL, from about 100 ng/ml to about 1,200 ng/mL, from about 100 ng/mL to about 1,000 ng/mL, from about 200 ng/mL to about 2,000 ng/mL, from about 200 ng/ml to about 1,800 ng/ml, from about 200 ng/mL to about 1,600 ng/mL, from about 200 ng/mL to about 1,400 ng/mL, from about 200 ng/ml to about 1,200 ng/mL, from about 200 ng/mL to about 1,000 ng/mL, from about 400 ng/ml to about 2,000 ng/mL, from about 400 ng/mL to about 1,800 ng/ml, from about 400 ng/ml to about 1,600 ng/mL, from about 400 ng/mL to about 1,400 ng/mL, from about 400 ng/ml to about 1,200 ng/mL, from about 400 ng/mL to about 1,000 ng/mL, from about 600 ng/mL to about 2,000 ng/mL, from about 600 ng/mL to about 1,800 ng/mL, from about 600 ng/ml to about 1,600 ng/mL, from about 600 ng/mL to about 1,400 ng/mL, from about 600 ng/ml to about 1,200 ng/mL, from about 600 ng/mL to about 1,000 ng/mL, from about 800 ng/mL to about 2,000 ng/mL, from about 800 ng/mL to about 1,800 ng/mL, from about 800 ng/mL to about 1,600 ng/mL, from about 800 ng/mL to about 1,400 ng/mL, from about 800 ng/ml to about 1,200 ng/mL, from about 800 ng/mL to about 1,000 ng/mL of lamotrigine in the subject, or any sub-range thereof.

In some embodiments, the administration of the ready to use non-aqueous solutions of lamotrigine results in an AUC value from 35,000 ng/ml*hr to about 40,000 ng/ml*hr of lamotrigine in the subject, or any sub-range thereof. For example, in some embodiments, the administration of the ready to use non-aqueous solutions of lamotrigine results in an AUC value from about 10,000 ng/mL*hr to about 100,000 ng/mL*hr, from about 10,000 ng/ml*hr to about 90,000 ng/mL*hr, from about 10,000 ng/mL*hr to about 80,000 ng/mL*hr, from about 10,000 ng/mL*hr to about 70,000 ng/mL*hr, from about 10,000 ng/mL*hr to about 60,000 ng/mL*hr, from about 10,000 ng/mL*hr to about 50,000 ng/mL*hr, from about 10,000 ng/ml*hr to about 40,000 ng/mL*hr, from about 20,000 ng/mL*hr to about 100,000 ng/mL*hr, from about 20,000 ng/mL*hr to about 90,000 ng/mL*hr, from about 20,000 ng/ml*hr to about 80,000 ng/mL*hr, from about 20,000 ng/mL*hr to about 70,000 ng/ml*hr, from about 20,000 ng/ml*hr to about 60,000 ng/mL*hr, from about 20,000 ng/mL*hr to about 50,000 ng/mL*hr, from about 20,000 ng/mL*hr to about 40,000 ng/ml*hr, from about 30,000 ng/ml*hr to about 100,000 ng/mL*hr, from about 30,000 ng/mL*hr to about 90,000 ng/ml*hr, from about 30,000 ng/mL*hr to about 80,000 ng/mL*hr, from about 30,000 ng/ml*hr to about 70,000 ng/ml*hr, from about 30,000 ng/mL*hr to about 60,000 ng/ml*hr, from about 30,000 ng/mL*hr to about 50,000 ng/mL*hr, from about 30,000 ng/ml*hr to about 40,000 ng/mL*hr, from about 35,000 ng/mL*hr to about 100,000 ng/mL*hr, from about 35,000 ng/ml*hr to about 90,000 ng/mL*hr, from about 35,000 ng/ml*hr to about 80,000 ng/ml*hr, from about 35,000 ng/ml*hr to about 70,000 ng/mL*hr, from about 35,000 ng/mL*hr to about 60,000 ng/mL*hr, from about 35,000 ng/mL*hr to about 50,000 ng/ml*hr, or from about 35,000 ng/ml*hr to about 40,000 ng/mL*hr of lamotrigine in the subject, or any sub-range thereof.

Furthermore, the present disclosure provides pharmaceutical compositions, which include the ready to use non-aqueous solutions including as an active component an effective dose of lamotrigine and a customary pharmaceutically acceptable carrier, i.e., one or more pharmaceutically acceptable carrier substances and/or additives.

Thus, the present disclosure provides, for example, the ready to use non-aqueous solutions of lamotrigine for use as pharmaceutical compositions, which comprise as active component an effective dose of lamotrigine and a customary pharmaceutically acceptable carrier, and the uses of lamotrigine in the therapy or prophylaxis of the above-mentioned diseases or disorders, e.g., neurological disorders or mental disorders, as well as their use for preparing medicaments for these purposes.

The pharmaceutical compositions according to the disclosure can be administered orally. Administration can also be carried out parenterally, for example subcutaneously, intramuscularly or intravenously for injection or infusion.

The amount of lamotrigine in the pharmaceutical composition may be from about 0.01 to about 700 mg, or from about 0.1 to about 200 mg, or from about 1 to about 200 mg, per dose, but depending on the type of the pharmaceutical composition, it can also be higher. In some embodiments, the amount of lamotrigine in the pharmaceutical composition is from 0.01 to 10 mg per dose. The pharmaceutical compositions may include from about 0.5 to about 90 percent by weight of lamotrigine. For this purpose, the ready to use non-aqueous solution of lamotrigine, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form, which can then be used as a pharmaceutical in human or veterinary medicine.

Besides the active compounds and carriers, the pharmaceutical compositions can also contain customary additives, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents and/or antioxidants.

One or more additional pharmacologically active agents may be administered in combination with the ready to use non-aqueous solution of lamotrigine. The additional pharmacologically active agent may include, for example, anticonvulsants, antipsychotics, antimanics, valproate, carbamazepine, clozapine, phenytoin, phenobarbital, primidone, and combinations thereof. An additional active agent (or agents) is intended to mean a pharmaceutically active agent (or agents) that is active in the body, including pro-drugs that convert to pharmaceutically active form after administration, which are different from lamotrigine. The additional active agents also include free-acid, free-base and pharmaceutically acceptable salts of said additional active agents. Generally, any suitable additional active agent or agents, including chemotherapeutic agents or therapeutic antibodies, may be used in any combination with the ready to use non-aqueous solution of lamotrigine in a single dosage formulation (e.g., a fixed dose drug combination), or in one or more separate dosage formulations which allows for concurrent or sequential administration of the active agents (co-administration of the separate active agents) to subjects. In addition, the ready to use non-aqueous solution of lamotrigine can be administered in combination with radiation therapy, hormone therapy, surgery or immunotherapy.

The present application also provides methods for combination therapies in which the additional active agent is known to modulate other pathways, or other components of the same pathway, or even overlapping sets of target enzymes which are used in combination with the ready to use non-aqueous solution of lamotrigine. In one embodiment, such therapy includes, but is not limited to, the combination of the ready to use non-aqueous solution of lamotrigine with chemotherapeutic agents, immunotherapeutic agents, hormonal and anti-hormonal agents, targeted therapy agents, and anti-angiogenesis agents, to provide a synergistic or additive therapeutic effect. In another embodiment, such therapy includes radiation treatment to provide a synergistic or additive therapeutic effect.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors.

The ready to use non-aqueous solutions of lamotrigine can be used in combination with the agents disclosed herein or other suitable agents, depending on the condition being treated. Hence, in some embodiments, the ready to use non-aqueous solutions of lamotrigine will be co-administered with other agents as described above. When used in combination therapy, the ready to use non-aqueous solutions of lamotrigine described herein are administered with the second agent simultaneously or separately. This administration in combination can include simultaneous administration of the two agents in the same dosage form, simultaneous administration in separate dosage forms, and separate administration. That is, the ready to use non-aqueous solutions of lamotrigine and any of the agents described above can be formulated together in the same dosage form and administered simultaneously. Alternatively, the ready to use non-aqueous solutions of lamotrigine and any of the agents described above can be simultaneously administered, wherein both the agents are present in separate formulations. In another alternative, the ready to use non-aqueous solutions of lamotrigine can be administered just followed by and any of the agents described above, or vice versa. In some embodiments of the separate administration protocol, the ready to use non-aqueous solutions of lamotrigine and any of the agents described above are administered a few minutes apart, or a few hours apart, or a few days apart. The ready to use non-aqueous lamotrigine solution may be administered at different frequencies such as, for example, from 1 to 20 times per week (or any number therein), from 1 to 90 times per month (or any number therein). For example, the ready to use non-aqueous lamotrigine solution may be administered once per day, twice per day, three times per day, or more than three times per day. The ready to use non-aqueous lamotrigine solution is administered for various durations such as, for example, a week, a month, two months, a year, or more than a year. For example, in some embodiments, the ready to use non-aqueous lamotrigine solution is administered every day for a week, every day for a month, every day for two months, every day for a year, or every day for more than a year.

In some embodiments, the ready to use non-aqueous solution of lamotrigine is administered every day or intermittently. In some embodiments, the administration according to the methods of the disclosure is for at least one treatment cycle. In some embodiments, the ready to use non-aqueous solution of lamotrigine is administered every day, intermittently, or once during a treatment cycle.

In some embodiments, a treatment cycle is 1-365 days. In an embodiment, a treatment cycle is 1 day, 2 days, one week (i.e., 7 days), 2 weeks (i.e., 14 days), 3 weeks (i.e., 21 days), 4 weeks (i.e., 28 days), 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks, one month, 2 months, 3 months, 6 months or about one year. As used herein, a "week" means seven consecutive days.

In some embodiments, the administration is for 1 treatment cycle. In some embodiments, the administration is for at least one treatment cycle and one additional treatment cycle (i.e., at least two treatment cycles). In some embodiments, the administration is for at least 2 treatment cycles, or at least 3 treatment cycles, or at least 4 treatment cycles, or at least 5 treatment cycles, or at least 6 treatment cycles, or at least 7 treatment cycles, or at least 8 treatment cycles, or at least 9 treatment cycles, or at least 10 treatment cycles, or at least 11 treatment cycles, or at least 12 treatment cycles, or at least 15 treatment cycles, or at least 20 treatment cycles, or at least 25 treatment cycles, or at least 30 treatment cycles, or at least 35 treatment cycles, or at least 40 treatment cycles. In some embodiments, the treatment is continuous until an endpoint which may be determined by a medical professional. In some embodiments, the administration is for less than or equal to 35 treatment cycles.

In some embodiments, the administered amount of an active agent of the disclosure is held constant during one treatment cycle. In some embodiments, the administered amount of an active agent of the disclosure is held constant for at least one treatment cycle and at least one additional treatment cycle (i.e., more than one treatment cycle). In some embodiments, the administered amount of an active agent of the disclosure can be increased in a second or subsequent treatment cycle (i.e., an additional treatment cycle). In some embodiments, the administered amount of an active agent of the disclosure can be held constant for at least two treatment cycles and decreased in a third or subsequent treatment cycle. In some embodiments, the administered amount of an active agent of the disclosure can be held constant for at least two treatment cycles and increased in a third or subsequent treatment cycle.

In some embodiments, the ready to use non-aqueous solution of lamotrigine is administered once a day on each day of a treatment cycle. In some embodiments, the ready to use non-aqueous solution of lamotrigine is administered intermittently during a treatment cycle.

Examples of additional non-limiting embodiments of the disclosure are provided in the following.

The ready to use non-aqueous solution according to any of the embodiments of the disclosure, wherein the ready to use non-aqueous solution comprises lamotrigine, wherein the n ready to use on-aqueous solution has at least one of the following properties: the ready to use non-aqueous solution has a turbidity ranging from about 0 NTU to about 20 NTU, the ready to use non-aqueous solution is a clear and colorless to light yellow liquid, and the ready to use non-aqueous solution does not form a precipitate or a suspension when stored at standard temperature and pressure for at least 7 days.

The ready to use non-aqueous solution according to any of the embodiments of the disclosure, wherein the ready to use non-aqueous solution has at least two of the following properties: the ready to use non-aqueous solution has a turbidity ranging from about 0 NTU to about 20 NTU, the ready to use non-aqueous solution is a clear and colorless to light yellow liquid, and the ready to use non-aqueous solution does not form a precipitate or a suspension when stored at standard temperature and pressure for at least 7 days.

The ready to use non-aqueous solution according to any of the embodiments of the disclosure, wherein the ready to use non-aqueous solution has all of the following properties: the ready to use non-aqueous solution has a turbidity ranging from about 0 NTU to about 20 NTU, the ready to use non-aqueous solution is a clear and colorless to light yellow liquid, and the ready to use non-aqueous solution does not form a precipitate or a suspension when stored at standard temperature and pressure for at least 7 days.

The ready to use non-aqueous solution according to any of the embodiments of the disclosure, wherein the ready to use non-aqueous solution has a turbidity ranging from about 0 NTU to about 15 NTU.

The ready to use non-aqueous solution according to any of the embodiments of the disclosure, wherein the ready to use non-aqueous solution has a turbidity ranging from about 0 NTU to about 10 NTU.

The ready to use non-aqueous solution according to any of the embodiments of the disclosure, wherein the ready to use non-aqueous solution has a turbidity ranging from about 0 NTU to about 5 NTU.

The ready to use non-aqueous solution according to any of the embodiments of the disclosure, wherein the ready to use non-aqueous solution comprises a pharmaceutically effective amount of lamotrigine.

The ready to use non-aqueous solution according to any of the embodiments of the disclosure, wherein the ready to use non-aqueous solution comprises lamotrigine at a concentration from about 1 mg/mL to about 40 mg/mL, about 10 mg/mL to about 30 mg/mL, or about 15 mg/mL to about 25 mg/mL by total volume of the ready to use non-aqueous solution.

The ready to use non-aqueous solution according to any of the embodiments of the disclosure, wherein the ready to use non-aqueous solution comprises an amount of propylene glycol ranging from about 1 weight % to about 99.9 weight % of by total weight of the ready to use non-aqueous solution.

The ready to use non-aqueous solution according to any of the embodiments of the disclosure, wherein the ready to use non-aqueous solution further comprises an amount of glycerin ranging from about 5 weight % to about 95 weight % of by total weight of the ready to use non-aqueous solution.

The ready to use non-aqueous solution according to any of the embodiments of the disclosure, wherein the ready to use non-aqueous solution has equal to or less than about 20 weight % of water by total weight of the ready to use non-aqueous solution.

The ready to use non-aqueous solution according to any of the embodiments of the disclosure, wherein the ready to use non-aqueous solution has equal to or less than about 1 weight % of water by total weight of the ready to use non-aqueous solution.

The ready to use non-aqueous solution according to any of the embodiments of the disclosure, wherein the ready to use non-aqueous solution further comprises at least one chosen from glycerin, propylene glycol, polypropylene glycol, polyethylene glycol, and ethanol.

The ready to use non-aqueous solution according to any of the embodiments of the disclosure, wherein the ready to use non-aqueous solution further comprises at least one additive chosen from an antioxidant, a buffer, and a preservative.

The ready to use non-aqueous solution according to any of the embodiments of the disclosure, wherein the ready to use non-aqueous solution further comprises at least one additive chosen from 3-tert-butyl-4-hydroxyanisole, citric acid, ethylenediaminetetraacetic acid, ethyl maltol, propylparaben, and methylparaben.

The ready to use non-aqueous solution according to any of the embodiments of the disclosure, wherein the ready to use non-aqueous solution has a pH meter reading ranging from about 7 to about 8.

The ready to use non-aqueous solution according any of the embodiments of the disclosure, wherein the ready to use non-aqueous solution has a viscosity ranging from about 50 centipoise to about 500 centipoise.

The ready to use non-aqueous solution according to any of the embodiments of the disclosure, wherein the ready to use non-aqueous solution has a density ranging from about 1.0 g/mL centipoise to about 1.2 g/mL.

The ready to use non-aqueous solution according to any of the embodiments of the disclosure, wherein the ready to use non-aqueous solution comprises a total weight percent of, propylene glycol, glycerin, polypropylene glycol, polyethylene glycol, and ethanol ranging from about 80 weight % to about 100 weight % by total weight of the ready to use non-aqueous solution.

The ready to use non-aqueous solution according to any of the embodiments of the disclosure, wherein the ready to use non-aqueous solution comprises a total weight percent of propylene glycol, glycerin, polypropylene glycol, polyethylene glycol and ethanol ranging from about 90 weight % to about 100 weight % by total weight of the ready to use non-aqueous solution.

The ready to use non-aqueous solution according to any of the embodiments of the disclosure, wherein the ready to use non-aqueous solution comprises a total weight percent of, propylene glycol, glycerin, polypropylene glycol, polyethylene glycol, and ethanol ranging from about 95 weight % to about 100 weight % by total weight of the ready to use non-aqueous solution.

The ready to use non-aqueous solution according to any of the embodiments of the disclosure, wherein even if water is present in the amount of up to about 20 weight % by total weight of the ready to use non-aqueous solution, the ready to use non-aqueous solution does not form a precipitate for up to 7 days of storage at standard temperature and pressure.

The ready to use non-aqueous solution according to any of the embodiments of the disclosure, wherein even if water is present in the amount of from about 10 weight % to about 20 weight % by total weight of the ready to use non-aqueous solution, the ready to use non-aqueous solution does not form a precipitate for up to 7 days of storage at standard temperature and pressure.

The ready to use non-aqueous solution according to any of the embodiments of the disclosure, wherein ready to use non-aqueous solution contains equal to or less than 10 weight % of sugar by total weight of the ready to use non-aqueous solution.

The ready to use non-aqueous solution according to any of the embodiments of the disclosure, wherein the ready to use non-aqueous solution contains equal to or less than about 10 weight % of sucrose by total weight of the ready to use non-aqueous solution.

The ready to use non-aqueous solution according to any of the embodiments of the disclosure, wherein the ready to use non-aqueous solution does not contain sucrose.

A method for treating a neurological disorder or a mental disorder in a subject in need thereof, comprising administering to the subject the ready to use non-aqueous solution according to any of the preceding embodiments, wherein the ready to use non-aqueous solution includes a therapeutically effective amount of lamotrigine.

EXAMPLES

The following examples are provided for illustrative purposes only and are not intended to limit the scope of the disclosure.

Example 1

Solubilities of lamotrigine in various non-aqueous solvents and purified water were determined as shown below.

TABLE 1

| Solvent | Solubility (mg/mL) |
|---|---|
| Propylene Glycol | 40.18 |
| Glycerin | 20.24 |
| PEG 400 | >30 |
| Polypropylene glycol 400 | 10-20 |
| Purified water | 0.31 |

Example 2

1 g lamotrigine was added into 90 g propylene glycol. The combination was mixed until the lamotrigine was dissolved. Propylene glycol was added until the total volume of the solution was 100 mL. The solution was then mixed until the solution was uniform.

Example 3

1 g lamotrigine was added into 90 g glycerin. The combination was mixed until the lamotrigine was dissolved. Glycerin was added until the total volume of the solution was 100 mL. The solution was then mixed until the solution was uniform.

Example 4

A solvent mixture was prepared with 10/90 (w/w) propylene glycol/glycerin. 1 g of lamotrigine was added into 90 g of the 10/90 (w/w) propylene glycol/glycerin mixture. The combination was mixed until the lamotrigine was dissolved.

The solvent mixture was added until the total volume of the solution was 100 mL. The solution was then mixed until the solution was uniform.

Example 5

A solvent mixture was prepared with 10/90 (w/w) propylene glycol/glycerin. 0.01 g of 3-tert-butyl-4-hydroxyanisole (BHA) was added into 90 g of the solvent mixture and mixed until the BHA was dissolved. Then, 1 g of lamotrigine was added to the combination and mixed until the lamotrigine was dissolved. The solvent mixture was added until the total volume of the solution was 100 mL. The solution was then mixed until the solution was uniform.

Example 6

A solvent mixture was prepared with 10 g of propylene glycol and 50 g of glycerin. Then, 1 g of lamotrigine was added to the solvent mixture and mixed until it was dissolved. Next, glycerin was added until the total volume of the solution was 100 mL. Then, 1% citric acid and 0.1% EDTA were added to the 100 mL solution. The solution was then mixed until the solution was uniform.

Example 7

A solvent mixture was prepared with 10/90 (w/w) propylene glycol/glycerin. Then, 0.5 g of ethyl maltol was added into 240 g of the solvent mixture and mixed until it was dissolved. Next, 2.5 g of lamotrigine was added and mixed until it was dissolved. The solvent mixture was added until the total volume of the solution was 250 mL. The solution was then mixed until the solution was uniform.

Example 8

A solvent mixture was prepared with 10/90 (w/w) propylene glycol/glycerin. Then, 1.2 g of ethyl maltol was added into 700 g of the solvent mixture and mixed until it was dissolved. Next, 8 g of lamotrigine was added and mixed until it was dissolved. The solvent mixture was added until the total volume of the solution was 800 mL. The solution was then mixed until the solution was uniform.

Example 9

A solvent mixture was prepared with 25/75 (w/w) propylene glycol/glycerin. Then, 1.2 g of ethyl maltol was added into 700 g of the solvent mixture and mixed until it was dissolved. Next, 8 g of lamotrigine was added and mixed until it was dissolved. The solvent mixture was added until the total volume of the solution was 800 mL. The solution was then mixed until the solution was uniform.

Example 10

A solvent mixture was prepared with 40/60 (w/w) propylene glycol/glycerin. Then, 1.2 g of ethyl maltol was added into 700 g of the solvent mixture and mixed until it was dissolved. Next, 8 g of lamotrigine was added and mixed until it was dissolved. The solvent mixture was added until the total volume of the solution was 800 mL. The solution was then mixed until the solution was uniform.

Example 11

TABLE 2

| Materials | g/batch |
| --- | --- |
| Propylene glycol | 694 |
| Ethyl maltol | 2.4 |
| Lamotrigine | 24 |
| Glycerin | 639 (QS to 1.2 L) |
| Total | 1359.4 |

The ethyl maltol was added into propylene glycol in a clean container and mixed until it completely dissolved. Then, the lamotrigine was added into the container and mixed until dissolved. Next, the glycerin was added to reach a total volume of 1.2 L. The solution was then mixed until the solution was clear and uniform.

Example 12

Analogous procedures to those of Example 11 were used and, additionally, 0.1% w/v flavor was added to afford the formulations as shown below.

TABLE 3

| Materials | g/batch |
| --- | --- |
| Propylene glycol | 694 |
| Ethyl maltol | 2.4 |
| Lamotrigine | 24 |
| Cherry flavor | 1.2 |
| Glycerin | 640 (QS to 1.2 L) |
| Total | 1361.6 |

Example 13

Analogous procedures to those of Example 11 were used, and additionally, 1%, 10% or 5% w/v purified water was added to afford the formulations as shown below.

TABLE 4

| Materials | Sample 13A g/batch | Sample 13B g/batch | Sample 13C g/batch |
| --- | --- | --- | --- |
| Propylene glycol | 567 | 567 | 567 |
| Ethyl maltol | 2 | 2 | 2 |
| Lamotrigine | 20 | 20 | 20 |
| Purified water | 10 (1% w/v) | 100 (10% w/v) | 50 (5% w/v) |
| Glycerin | 529 (QS to 1.0 L) | 423 (QS to 1.0 L) | 494 (QS to 1.0 L) |
| Total | 1128 | 1112 | 1133 |

Example 14

Analogous procedures to those of Example 11 were used and, additionally, citric acid (0.02% w/v) was added to afford the formula below with 10% w/v purified water.

TABLE 5

| Materials | g/batch |
| --- | --- |
| Propylene glycol | 694 |
| Citric acid | 0.24 |
| Lamotrigine | 24 |
| Ethyl maltol | 2.4 |
| Purified water | 12 |
| Glycerin | 624 (QS to 1.2 L) |
| Total | 1356.6 |

Example 15

Analogous procedure to those of Example 14 were used, except the purified water was omitted.

TABLE 6

| Materials | g/batch |
| --- | --- |
| Propylene glycol | 694 |
| Citric acid | 0.24 |
| Lamotrigine | 24 |
| Glycerin | 634 (QS to 1.2 L) |
| Total | 1352.2 |

Example 16

Ready to use non-aqueous solutions having a lamotrigine concentration of 20 mg/mL were prepared with different ratios of propylene glycol and glycerin according to the following formulations.

TABLE 7

| Materials | Sample 16A g/batch | Sample 16B g/batch |
| --- | --- | --- |
| Propylene glycol | 694 | 960 |
| Ethyl maltol | 2.4 | 2.4 |

TABLE 7-continued

| Materials | Sample 16A g/batch | Sample 16B g/batch |
| --- | --- | --- |
| Lamotrigine | 24 | 24 |
| Glycerin | 638 (QS to 1.2 L) | 310 (QS to 1.2 L) |
| Total | 1358.4 | 1296.4 |

Sample 16A (51.1% w/w and/or 57.8% w/v propylene glycol, 47.0% w/w and/or 53.2 w/v glycerin)
Sample 16B (74.1% w/w and/or 80% w/v propylene glycol, 23.9% w/w and/or 25.8% w/v glycerin)

Example 17

Analogous procedures to those of Example 11 were used and, additionally, D&C yellow #10 (0.00067 mg/mL) was added to afford the formulations below.

TABLE 8

| Materials | g/batch |
| --- | --- |
| Propylene glycol | 694 |
| Ethyl maltol | 2.4 |
| Lamotrigine | 24 |
| D&C Yellow #10 | 0.0008 |
| Glycerin | 638 (QS to 1.2 L) |
| Total | 1358.4 |

Example 18

Ready to use non-aqueous solutions having a lamotrigine concentration of 20 mg/mL were prepared with different ratios of propylene glycol and glycerin as shown in the formulations below.

TABLE 9

| Materials | Sample g/batch | Sample 18A % w/w | Sample 18C % w/v | Sample g/batch | Sample 18B % w/w | Sample 18D % w/v |
| --- | --- | --- | --- | --- | --- | --- |
| Propylene glycol | 123 | 9.9 | 12.3 | 936 | 86.7 | 93.6 |
| Ethyl maltol | 2 | 0.16 | 0.2 | 2 | 0.19 | 0.2 |
| Lamotrigine | 20 | 1.6 | 2.0 | 20 | 1.9 | 2.0 |
| Glycerin | 1102.7 (QS to 1.0 L) | 88.4 | 110.3 | 122 (QS to 1.0 L) | 11.3 | 12.2 |
| Total | 1247.7 | 100 g | 100 mL | 1080 | 100 g | 100 mL |

Sample 18A (9.9% w/w and/or 12.3% w/v propylene glycol, 88.4% w/w and/or 110.3% w/v glycerin)
Sample 18B (86.7 w/w and/or 93.6% w/v propylene glycol, 11.3% w/w and/or 12.2 w/v glycerin)

Example 19

TABLE 10

| Materials | Sample 19A g/batch | Sample 19B g/batch |
| --- | --- | --- |
| Propylene glycol | 231.3 | 231.3 |
| Purified water | 80 | 120 |

TABLE 10-continued

| Materials | Sample 19A g/batch | Sample 19B g/batch |
|---|---|---|
| Lamotrigine | 8 | 8 |
| Glycerin | 118 (QS to 400 ml) | 80 (QS to 400 ml) |
| Total | 437.3 | 439.3 |

Sample 19A: 20% w/v purified water in formula, no precipitation in 7 days

Sample 19B: 30% w/v purified water in formula, precipitation forms in 7 days

Example 20

Analogous procedures to those of Example 11 were used and, additionally, propylparaben (0.02% w/v) and methylparaben (0.18% w/v) were added to afford the formulation below.

TABLE 11

| Materials | g/batch |
|---|---|
| Propylene glycol | 694 |
| Lamotrigine | 24 |
| Sucralose | 12 |
| Ethyl maltol | 2.4 |
| Propylparaben | 0.24 |
| Methylparaben | 2.16 |
| Glycerin | 637 (QS to 1.2 L) |
| Total | 1371.8 |

Example 21

Analogous procedures to those of Example 11 were used and, additionally, alcohol, D&C yellow #10, sucralose and berry flavor are added to afford the formulations below.

TABLE 12

| Materials | g/batch |
|---|---|
| Propylene glycol | 694 |
| Alcohol | 100 |
| Ethyl maltol | 1.5 |
| Lamotrigine | 20 |
| D&C Yellow #10 | 0.0005 |

TABLE 12-continued

| Materials | g/batch |
|---|---|
| Sucralose | 5.0 |
| Berry Flavor | 2.0 |
| Glycerin | 250 (QS to 1.0 L) |
| Total | 1072.5 |

Example 22

A single dose fasting pharmacokinetic study was performed using the ready to use non-aqueous solution. The ready to use non-aqueous solution had a composition as shown in Table 13.

TABLE 13

| Ingredient | Concentration, mg/mL | Concentration, % w/v | Concentration, % w/w |
|---|---|---|---|
| Lamotrigine | 20 | 2.0 | 1.77 |
| Propylene Glycol | 578 | 57.8 | 51.15 |
| Ethyl Maltol | 2 | 0.2 | 0.18 |
| Glycerin | 530 | 53.0 | 46.90 |

An open label, randomized, three-period, three-treatment [Treatment A (Test product administration under fasting condition) vs. Treatment B (Reference product (LAMICTAL) administration under fasting condition) and Treatment C (Test product administration under fed condition) vs. Treatment A (Test product administration under fasting condition)], three-sequence, crossover, balanced, single dose oral clinical pharmacokinetic (fasting condition bioequivalence and food effect) study in healthy adult human subjects was conducted to evaluate the oral fasting bioequivalence of the test formulation relative to the reference formulation and to evaluate the food effect of the test formulation under fed condition relative to the fasting condition.

A dosage of 50 mg of lamotrigine (equivalent to 2.5 mL of the ready to use non-aqueous solution) was used in the treatment A (fasted state) and treatment C (fed state) and the results were compared with that using 2×25 mg (50 mg) of LAMICTAL (lamotrigine) tablets in treatment B (fasted state). Subjects in treatments A and B were fasted for at least ten hours prior to dosing until at least four hours after dosing while water intake was restricted for at least one hour prior to dosing until at least one hour after dosing, except that water was given to the subjects upon dosing of the LAMICTAL (lamotrigine) tablets.

The administration was carried out in healthy adult human subjects at a randomized schedule in each period of the study. The results are provided in FIGURE and Table 14 below, showing bioequivalence (BE) of the ready to use non-aqueous solution compared with the LAMICTAL (lamotrigine) tablets. The $C_{max}$, $AUC_t$, and $AUC_i$ values are each in natural logarithmic form (Ln) and time t is 168 hours.

TABLE 14

| | BE (Test Fast (A) vs Reference Fast (B)) | | | Food effect Assessment (Test Fed (C) vs Test Fast (A)) | | |
|---|---|---|---|---|---|---|
| | Ln(Cmax) | Ln(AUCt) | Ln(AUCi) | Ln(Cmax) | Ln(AUCt) | Ln(AUCi) |
| | | | | Dependent Units | | |
| | (ng/mL) | (ng/mL)*(hr) | (ng/mL)*(hr) | (ng/mL) | (ng/mL)*(hr) | (ng/mL)*(hr) |
| | | | | Test | | |
| | A | A | A | C | C | C |
| Geometric Least Square Mean of Reference Formulation | 793.702 | 32551.030 | 33976.931 | 882.787 | 34707.336 | 36224.076 |
| Geometric Least Square Mean of Test Formulation | 882.072 | 34646.834 | 36154.915 | 701.271 | 33686.799 | 35105.932 |
| % Ratio | 111.13 | 106.44 | 106.41 | 79.44 | 97.06 | 96.91 |
| CI_90_Lower | 106.51 | 103.78 | 103.59 | 75.99 | 94.31 | 93.98 |
| CI_90_Upper | 115.95 | 109.16 | 109.31 | 83.05 | 99.89 | 99.94 |
| Power | 0.9984 | 1.0000 | 1.0000 | 0.0282 | 1.0000 | 1.0000 |
| Coefficient of Variation | 11.140 | 6.623 | 7.035 | 11.808 | 7.625 | 8.165 |

Note:
The reported power is based on Schuirmann's TOST (Two One Sided Test) confidence interval approach.

Example 23

A stability study was performed using the ready to use non-aqueous solutions having water contents of 1% w/w, 5% w/w, and 10% w/w. While water was present, water did not function as a solvent. The results are provided in Table 15 below, all showing excellent stability. Impurity A is 3-amino-6-(2,3-dichlorophenyl)-1,2,4-triazin-5 (4H)-one.

TABLE 15

| | Initial | 3 months/ 25° C./60% humidity | 2 months/ 40° C./75% humidity | 3 months/ 40° C./75% humidity |
|---|---|---|---|---|
| 1% w/w purified water | | | | |
| Impurity A (% w/w) | 0.008 | 0.02 | 0.07 | 0.11 |
| Total Impurities (% w/w) | 0.02 | 0.02 | 0.11 | 0.19 |
| Lamotrigine (% w/w) | 100 | 99.0 | 99.7 | 97.9 |
| 5% w/w purified water | | | | |
| Impurity A (% w/w) | 0.011 | 0.05 | 0.17 | 0.26 |
| Total Impurities (% w/w) | 0.02 | 0.05 | 0.21 | 0.32 |
| Lamotrigine (% w/w) | 99.9 | 99.1 | 100.1 | 99.1 |

| Materials | Sample 24A (10:90) | Sample 24B (25:75) | Sample 24C (40:60) |
|---|---|---|---|
| Propylene glycol | 97 g | 236 g | 369 g |
| Glycerin | 875 g | 706 g | 554 g |
| Ethyl maltol | 1.2 g | 1.2 g | 1.2 g |
| Lamotrigine | 8 g | 8 g | 8 g |
| Total | | 800 mL | |

| 10% w/w purified water | | | | |
|---|---|---|---|---|
| Impurity A (% w/w) | 0.013 | 0.07 | 0.27 | 0.43 |
| Total Impurities (% w/w) | 0.02 | 0.07 | 0.31 | 0.49 |
| Lamotrigine (% w/w) | 100 | 98.9 | 99.7 | 98.2 |

Example 24

A stability study was performed using the ready to use non-aqueous solutions having various propylene glycol to glycerin weight ratios as shown in Table 16 below.
Table 16

Ethyl maltol was added to propylene glycol in a clean container and mixed until completely dissolved. Then lamotrigine was added into the container and mixed until dissolved. Next, the glycerin was added to make up the final volume to 800 mL. The solution was then mixed until it was clear and uniform. The results are provided in Table 17 below, all showing excellent stability. Impurity A is 3-amino-6-(2,3-dichlorophenyl)-1,2,4-triazin-5 (4H)-one.

TABLE 17

| | Initial | 1 month/ 25° C./60% RH | 2 months/ 25° C./60% RH | 3 months/ 25° C./60% RH |
|---|---|---|---|---|
| Sample 24A (10:90) | | | | |
| Impurity A (% w/w) | 0.09 | 0.13 | 0.10 | 0.14 |
| Total Impurities (% w/w) | 0.25 | 0.29 | 0.37 | 0.40 |
| Lamotrigine (% w/w) | 98.6 | 99.0 | 98.6 | 98.6 |
| Sample 24B (25:75) | | | | |
| Impurity A (% w/w) | 0.10 | 0.12 | 0.10 | 0.13 |
| Total Impurities (% w/w) | 0.26 | 0.26 | 0.32 | 0.34 |
| Lamotrigine (% w/w) | 98.5 | 99.0 | 98.5 | 98.5 |
| Sample 24C (40:60) | | | | |
| Impurity A (% w/w) | 0.10 | 0.12 | 0.09 | 0.12 |
| Total Impurities (% w/w) | 0.27 | 0.24 | 0.25 | 0.27 |
| Lamotrigine (% w/w) | 98.5 | 98.4 | 98.5 | 98.5 |

While the disclosure has been described above with reference to specific embodiments thereof, it is apparent that many changes, modification, and variations can be made without departing from the concept disclosed herein. Accordingly, it is intended to embrace all such changes, modifications, and variations that fall within the spirit and broad scope of the appended claims.

What is claimed is:

1. A ready to use solution, comprising lamotrigine dissolved in a solvent,
   wherein the solvent comprises propylene glycol and at least one co-solvent comprising glycerin,
   wherein the ready to use solution has a water content of equal to or less than about 20% w/w of the ready to use solution, and
   wherein water is not the at least one co-solvent.

2. The ready to use solution of claim 1, wherein a concentration of lamotrigine in the ready to use solution is about 0.01 mg/mL to about 40 mg/mL.

3. The ready to use solution of claim 1, wherein a concentration of lamotrigine in the ready to use solution is about 20 mg/mL.

4. The ready to use solution of claim 1, wherein the water content is equal to or less than about 1% w/w of the ready to use solution.

5. The ready to use solution of claim 1, wherein the at least one co-solvent further comprises at least one selected from the group consisting of polypropylene glycol, polyethylene glycol, and ethanol.

6. The ready to use solution of claim 1, wherein water is not present in the ready to use solution.

7. The ready to use solution of claim 1, wherein a weight ratio of propylene glycol to glycerin is 80:20 to 20:80.

8. The ready to use solution of claim 1, wherein a propylene glycol content is about 45% to about 87% w/w of the ready to use solution.

9. The ready to use solution of claim 1, wherein a glycerin content is about 11% to about 60% w/w of the ready to use solution.

10. The ready to use solution of claim 1, wherein a propylene glycol content is about 45% to about 55% w/w of the ready to use solution and a glycerin content is about 45% to about 55% w/w of the ready to use solution.

11. The ready to use solution of claim 1, further comprising ethyl maltol.

12. The ready to use solution of claim 1, wherein the ready to use solution has a pH meter reading from about 7.5 to about 7.8.

13. The ready to use solution of claim 1, wherein the ready to use solution has a viscosity from 200 centipoise to about 300 centipoise.

14. The ready to use solution of claim 1, wherein the ready to use solution has a density from about 1.1 g/mL to about 1.2 g/mL.

15. A ready to use solution, comprising:
   about 15 mg/mL to about 25 mg/mL of lamotrigine; and
   a solvent, the solvent comprising:
      about 45% to about 55% w/w of propylene glycol; and
      about 45% to about 55% w/w of glycerin,
   wherein the ready to use solution has a water content of equal to or less than about 20% w/w of the ready to use solution, and
   wherein water is not the solvent.

16. The ready to use solution of claim 15, wherein a concentration of lamotrigine in the ready to use solution is about 20 mg/mL.

17. A method for treating a disorder, comprising administering orally to a human subject in need thereof a ready to use solution, wherein the ready to use solution includes about 2 mg to about 700 mg of lamotrigine dissolved in a solvent, wherein the solvent comprises propylene glycol and at least one co-solvent comprising glycerin, wherein the ready to use solution has a water content of equal or less than about 20% w/w of the ready to use solution, wherein water is not the at least one co-solvent, and wherein the disorder is epilepsy or bipolar disorder.

18. The method of claim 17, wherein the disorder is epilepsy.

19. The method of claim 17, wherein the disorder is bipolar disorder.

20. The method of claim 18, wherein the epilepsy disorder includes partial seizures, tonic-clonic seizures, and/or seizures of Lennox-Gastaut syndrome.

21. The method of claim 19, wherein the bipolar disorder is a bipolar I disorder.

22. The method of claim 17, comprising administering about 2 mg to about 500 mg of lamotrigine.

23. The method of claim 17, wherein the administering results in a $C_{max}$ value from about 800 ng/ml to about 1,000 ng/ml of lamotrigine in the subject.

24. The method of claim 17, wherein the administering results in an AUC value from about 35,000 ng/mL*hr to about 40,000 ng/mL*hr of lamotrigine in the subject.

25. The method of claim 21, wherein the therapeutically effective amount is administered after fasting.

26. The method of claim 21, wherein the therapeutically effective amount is administered after a meal.

27. The method of claim 17, wherein a concentration of lamotrigine in the ready to use solution is about 0.01 mg/mL to about 40 mg/mL.

28. The method of claim 17, wherein a concentration of lamotrigine in the ready to use solution is about 20 mg/mL.

29. The method of claim 17, wherein water is not present in the ready to use solution.

30. The method of claim 17, wherein a propylene glycol content is about 45% to about 55% w/w of the ready to use solution and a glycerin content is about 45% to about 55% w/w of the ready to use solution.

* * * * *